United States Patent [19]

Bedford

[11] Patent Number: 4,887,994
[45] Date of Patent: Dec. 19, 1989

[54] APPLICATOR SWABS AND METHOD OF MAKING SAME

[76] Inventor: Peter H. Bedford, 3817 Mistral Ave., Huntington Beach, Calif. 92649

[21] Appl. No.: 216,315

[22] Filed: Jul. 6, 1988

[51] Int. Cl.$^4$ .............................................. A61M 35/00
[52] U.S. Cl. .......................................... 604/1; 604/2; 604/3; 604/305; 604/306; 15/244.1; 132/317; 132/318; 132/320; 206/210; 206/229; 206/361; 206/438; 206/467; 206/470
[58] Field of Search ....................... 132/317, 320, 393; 206/210, 229, 361, 438, 570; 401/1, 3, 132, 196; 604/1, 2, 15, 162, 304, 305, 306; 15/244.1

[56] References Cited

U.S. PATENT DOCUMENTS

| | | | |
|---|---|---|---|
| 2,218,738 | 10/1940 | Boysen | 604/1 X |
| 2,987,063 | 6/1961 | Glickston | 604/1 |
| 3,103,682 | 9/1963 | Markle | 604/1 X |
| 3,179,108 | 4/1965 | Bloch et al. | 604/1 |
| 3,228,398 | 1/1966 | Leonard et al. | 604/1 |
| 3,463,302 | 8/1969 | Preston | 206/361 |
| 3,508,547 | 4/1970 | Deuschle | 604/1 |
| 3,759,375 | 9/1973 | Nappi | 206/210 X |
| 4,740,194 | 4/1988 | Barabino et al. | 401/132 X |

Primary Examiner—Richard J. Apley
Assistant Examiner—N. Paul
Attorney, Agent, or Firm—Price, Gess & Ubell

[57] ABSTRACT

An applicator and/or scrub saturated with a desired fluid is packaged in a sealed, liquid-impervious pouch. The liquid-carrying applicator or scrub is made from open-cell, polyurethane foam. A cylinder of the foam is mounted on a stick. The tip end of the foam applicator is fastened to the tip of the stick in a manner that creates a rounded smooth tip. The tip end of the foam applicator may be formed into a smaller brush-like shape.

15 Claims, 2 Drawing Sheets

4,887,994

APPLICATOR SWABS AND METHOD OF MAKING SAME

BACKGROUND OF THE INVENTION

1. Field of the Invention

The present invention relates generally to improvements in stick mounted swabs, and more particularly pertains to a new and improved fluid laden swab and method of making the same.

2. Description of the Related Art

In the field of stick mounted swabs, it has been the practice to employ spun cotton wound on the end of a stick for cleaning and for carrying fluid to a specific area. Such devices have been unsatisfactory in that cotton is an organic material and creates a rejection reaction in the human body. The cotton fibers get caught in wounds when used for cleaning. The cotton swab itself is less than satisfactory in carrying fluids such as disinfectant to wounds on the body. The present invention overcomes these problems.

SUMMARY OF THE INVENTION

An open-cell, polyurethane foam is utilized to hold the fluid. The foam, preferably shaped as a cylinder, is glued to a stick handle so that the tip end of the foam is rounded and smooth, completely enclosing the end of the stick handle. A plurality of fluid saturated foam swabs are packaged in a liquid-impervious pouch. The pouch may have a second chamber containing additional application fluid. The tip end of the foam swabs may also be formed into a smaller brush-like shape for precision application work.

BRIEF DESCRIPTION OF THE DRAWINGS

The general objects and many of the attendant advantages of this invention will be readily appreciated as the same becomes better understood by reference to the following detailed description when considered in conjunction with the accompanying drawings, in which like reference numerals designate like parts throughout the figures thereof, and wherein.

DESCRIPTION OF THE PREFERRED EMBODIMENTS

Figure 2:
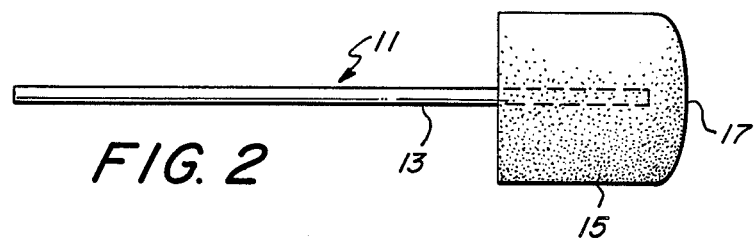
FIG. 2 is a side elevation of an applicator swab after assembly.

FIG. 2 illustrates a preferred embodiment of an applicator swab manufactured according to the present invention. Applicator swab 11 comprises a stick handle 13 and a foam applicator 15 that has a rounded end 17 which completely encloses the tip (not shown) of the stick handle 13. The foam applicator 15 is preferably an open cell polyurethane foam. The foam can have varying cell sizes, depending on whether a coarse or fine surface texture is desired. The coarse surface texture would be most advantageous for scrubbing and cleaning wounds, whereas a smaller cell structure providing a smoother surface would be utilized for the application of fluid such as disinfecting liquids to a wound, for example. Such fluids could be an iodine solution or other similar disinfectant fluid or cream.

Figure 1:
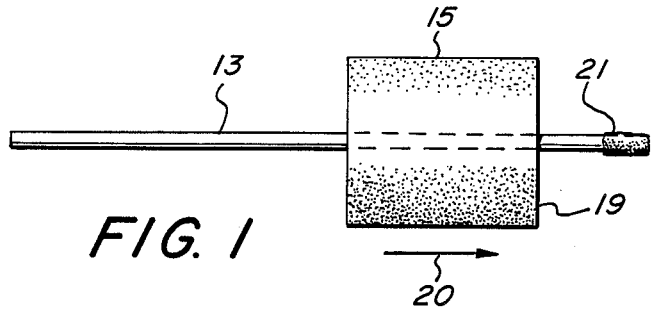
FIG. 1 is a side elevation of the parts of an applicator swab in the process of assembly.

The foam applicator 15 (FIG. 1) is essentially a cylinder of foam, having a circular cross-section. It may simply be stamped out of a pad of open cell polyurethane foam. The stick handle 13 may be made of plastic, wood or paper, or any other material, and may have any convenient length and cross-section, although a cylindrical handle is preferred.

There is a hole through the geometric center of the foam applicator 15 through which the stick handle 13 extends. After the foam member 15 is placed on the stick handle 13, a certain amount of glue 21 can be placed at the first tip end of stick handle 13. After this glue gets tacky, the foam member 15 is moved towards the tip having the end 21, causing end 19 of the foam 15 to engage the glue 21. This causes the foam end 19 to stick to the parts of the stick handle 13 covered with glue. As movement is continued in direction 20, the foam end 19 of applicator 15 closes in on itself, forming a rounded end 17, as shown in FIG. 2. This rounded end is highly desirable in an applicator, since it prevents the hard tip of stick handle 13 from coming in contact with sensitive wound surfaces or body tissue.

An appropriate glue 21, such as "STABON" glue made by the STABON Company or hot melt glue made by 3M or other manufacturers of hot melt glue, may be used. The same effect can be obtained by heat treatment of the tip end of stick handle 13 and the tip end 19 of foam applicator 15. The stick handle 13 in this case must be a plastic material. This heating can be done by thermal means or by ultrasonic means, as is well known, and will not be described herein.

Figure 3:
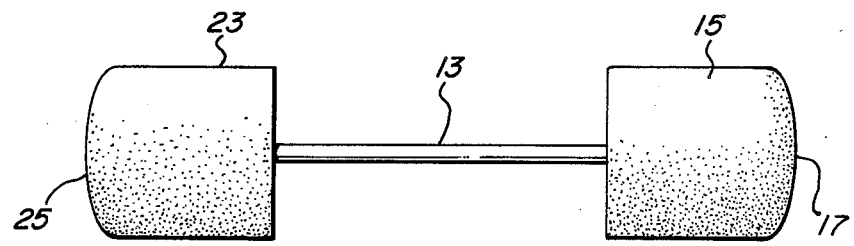
FIG. 3 is a side elevation of an applicator swab having an alternate embodiment.

Referring to FIG. 3, a dual applicator swab is illustrated wherein an additional foam applicator 23 is attached to the end opposite the end having applicator 15. Applicator 23 again has a rounded tip 25 formed in the manner above illustrated. This type of applicator is advantageously utilized in the medical profession for cleaning decubitus ulcers or other wound areas. A coarse foam pad 23 may be utilized to clean the dead tissue away. A foam applicator 15 containing a disinfectant fluid is used to apply it to the wound. Foam applicator 15 has a smaller cell structure and thereby is much softer and smoother.

Figure 4:
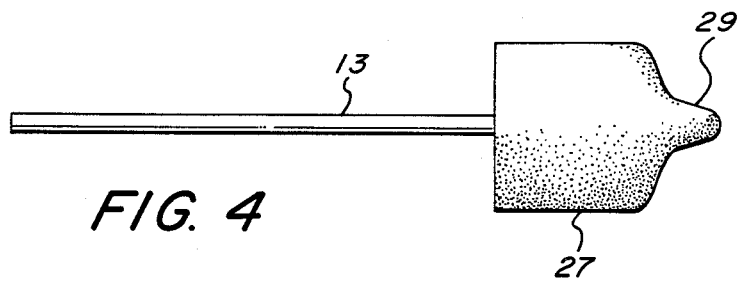
FIG. 4 is a side elevation of an applicator swab in another preferred embodiment.

Referring now to FIG. 4, an alternate preferred embodiment of an applicator swab according to the present invention is illustrated. The applicator comprises a foam body 27 mounted on a stick handle 13. The applicator body is further worked to form the tip end 29 into a conical paintbrush form. This is accomplished by heat treating the end to the point of collapsing the open cell foam structure and thereby forming the tip end, as illustrated. The type of applicator illustrated in FIG. 4 is useful for application of cosmetics, for example, and especially for application of a variety of fluids in a very precise manner by the conical-shaped tip 29. The body 21 of the foam applicator can still be used to apply bulk fluid or for removal of fluid.

When impregnated with an antibacterial or disinfectant fluid, the applicator swabs of the present invention are advantageously packaged in a fluid-impervious package or pouch 31. The pouch is sealed at its periphery to completely encase the plurality of applicator swabs 35, 37 and 39 contained therein. The pouch provides a disinfected environment for storage of the swabs 35, 37 and 39. The pouch may be opened by tearing along a tear line 33, for example, or by utilizing any other convenient opening device. The package 31 is preferably made of an aluminum foil material that is well known for this use.

Each of the applicators 35, 37 and 39 stored within the pouch 31 may contain an antigermicide or disinfectant solution 41, or any other solution that can be conveniently applied by a swab applicator of the type illustrated herein. Besides the solution contained within the open-cell foam applicators 35, 37 and 39, a certain amount of the solution might be found in the bottom of the pouch. This type of disinfected packaging of the applicator swabs is designed to encourage the swabs to be thrown away.

Applicator 35 is shown as having a flat stick handle 37, as distinguished from the cylindrical stick handles 13 of applicators 37 and 39. Flat stick handle 37 would be more advantageous for an applicator used to paint a fluid such as iodine onto a larger area of the body, for example.

Figure 6:
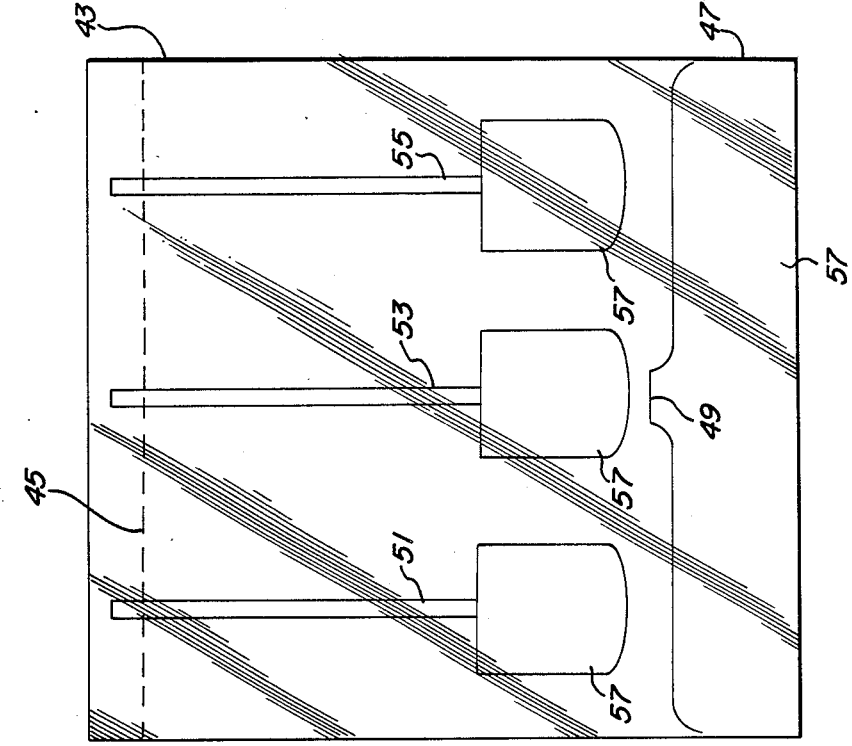
FIG. 6 is a side view illustrating a plurality of applicators in a liquid-impervious pouch of an alternate preferred embodiment.
Figure 5:
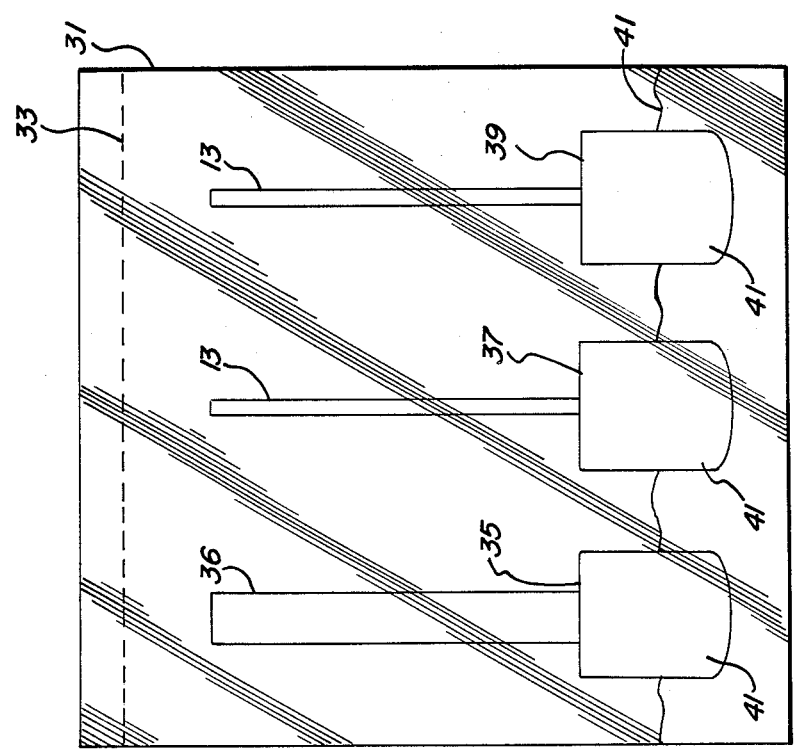
FIG. 5 is a side view of a plurality of applicators in a liquid-impervious pouch.

The application of medicinal fluids is not the only use that may be made of a package containing the applicator swabs of the present invention. Referring to FIG. 6, a package containing a plurality of applicator swabs 51, 53 and 55 is illustrated. The applicator swabs are saturated with a sunscreen lotion 57. The applicator swabs are contained within a fluid-impervious package 43 that is sealed around its perimeter. The package can be opened by tearing at a tear line 45, for example, or by other convenient means. The package 45 is shown as having an additional pouch 47 containing sunscreen lotion 57 therein. The pouch is separate from the main chamber of package 43, but has a weak interface 49 therebetween. By squeezing pouch 47, this interface 49 is broken allowing additional sunblock lotion 57 to be squeezed out. Thus, besides containing sunblock lotion within the foam applicators 51, 53 and 55, additional sunblock lotion contained in pouch 57 may be squeezed out as needed. Once all the lotion is used up, the individual applicators 51, 53 and 55 may be thrown away with the empty pouch 43.

This provides a very convenient and sanitary lotion package with disposal applicators which have a variety of uses, both in the medical and cosmetic fields.

What is claimed is:

1. An applicator and cleansing swab comprising:
   a stick handle to be held;
   a first three-dimensional piece of open-cell polyurethane foam mounted on the stick handle at a first end so that said handle pierces the foam material;
   glue on the first tip end of said handle fastening said first foam piece to said stick whereby the end of said foam adjacent to the tip of said handle is attached to said handle by the glue so that the tip of said handle is encased by the foam end;
   a second three-dimensional piece of open-cell, polyurethane foam material of coarser structure than said first piece, mounted on the stick handle at the second end so that said handle pierces the foam material;
   glue on the second tip end of said handle fastening said second foam piece to said stick whereby the end of said foam adjacent to the tip of said handle is attached to said handle by the glue so that the tip of said handle is encased by the foam end; and
   a disinfecting fluid contained within said first piece of open-cell foam whereby said second piece of foam at the second end of the said handle may be used to scrape and clean a wound and said first piece of foam at the first end of said handle is used to apply disinfecting fluid to the clean wound.

2. A fluid dispensing pack containing applicators therein comprising:
   a flexible envelope of liquid-impervious material, said envelope being sealed on all sides;
   a separate chamber in said envelope, containing topical application fluid separated from the envelope by a perforatable seal barrier; whereby squeezing said separate chamber will break the seal barrier causing topical application fluid therein to enter the envelope; and
   at least one applicator swab located in said envelope, said swab comprising:
      a stick handle to be held;
      a three-dimensional piece of foam mounted on the stick handle so that said handle pierces the foam material; and
   adhesion means on the tip of said handle fastening said foam to said stick whereby the end of said foam adjacent to the tip of said handle is attached to said handle by the adhesion means so that the tip of said handle is encased by the foam; and
   said three-dimensional piece of foam being saturated with a topical application fluid, said fluid being contained within said flexible envelope.

3. The applicator swab of claim 2 wherein said adhesion means comprises glue.

4. The applicator swab of claim 2, wherein said stick handle comprises a cylindrical length of plastic.

5. The applicator swab of claim 4 wherein said adhesion means comprises thermal heating of the tip of said foam and stick handle.

6. The applicator swab of claim 4 wherein said adhesion means comprises ultrasound heating of the tip of said foam and stick handle.

7. The applicator swab of claim 2 wherein said stick handle comprises a cylindrical length of paper.

8. The applicator swab of claim 2 wherein said stick handle comprises a cylindrical length of wood.

9. The applicator swab of claim 2 wherein said stick handle comprises a flat length of wood.

10. The applicator swab of claim 2 wherein said stick handle comprises a flat length of plastic.

11. The applicator swab of claim 2 wherein said foam material comprises a cylinder shape, said handle piercing the approximate geometric center of the foam cylinder and further comprising a tip end on the foam cylinder shaped into a brush and encasing the tip of said stick handle.

12. The fluid dispensing pack of claim 2 wherein said foam material comprises open-cell polyurethane foam in a cylinder shape and said handle pierces the approximate geometric center of the foam cylinder.

13. The fluid dispensing pack of claim 2 wherein said topical application fluid comprises an iodine solution.

14. The fluid dispensing pack of claim 2 wherein said topical application fluid comprises a sunscreen lotion.

15. The fluid dispensing pack of claim 14 wherein said foam cylinder has its tip end shaped into a brush which encases the tip of said stick handle.

* * * * *